(12) United States Patent
Lai et al.

(10) Patent No.: US 11,680,291 B2
(45) Date of Patent: Jun. 20, 2023

(54) PCR APPARATUS FOR REAL-TIME DETECTING OF ONE OR MORE FLUORESCENT SIGNALS

(71) Applicant: CREDO DIAGNOSTICS BIOMEDICAL PTE. LTD., Singapore (SG)

(72) Inventors: Ying-Ta Lai, New Taipei (TW); Yu-Cheng Ou, New Taipei (TW); Chun-Te Wu, New Taipei (TW); Yu-Wen Huang, New Taipei (TW); Han-Yi Chen, New Taipei (TW)

(73) Assignee: CREDO DIAGNOSTICS BIOMEDICAL PTE, LTD., Singapore (SG)

( * ) Notice: Subject to any disclaimer, the term of this patent is extended or adjusted under 35 U.S.C. 154(b) by 430 days.

(21) Appl. No.: 16/816,350

(22) Filed: Mar. 12, 2020

(65) Prior Publication Data
US 2020/0392559 A1    Dec. 17, 2020

(30) Foreign Application Priority Data

Jun. 13, 2019  (TW) .................................. 108120548

(51) Int. Cl.
| | | |
|---|---|---|
| *C12Q 1/686* | (2018.01) | |
| *B01L 7/00* | (2006.01) | |
| *C12N 15/11* | (2006.01) | |
| *G01N 21/64* | (2006.01) | |

(52) U.S. Cl.
CPC ............. *C12Q 1/686* (2013.01); *B01L 7/52* (2013.01); *C12N 15/11* (2013.01); *G01N 21/64* (2013.01)

(58) Field of Classification Search
CPC ......... C12Q 1/686; C12Q 1/6851; B01L 7/52; B01L 2300/0627; B01L 2300/0654; B01L 2300/18; C12N 15/11; G01N 21/64
See application file for complete search history.

(56) References Cited

U.S. PATENT DOCUMENTS

| | | |
|---|---|---|
| 2014/0178861 A1 | 6/2014 | Duer |
| 2015/0111287 A1 | 4/2015 | Rawle |
| 2016/0257992 A1 | 9/2016 | Tsukuda |
| 2016/0265030 A1 | 9/2016 | Tsukuda |
| 2017/0113221 A1 | 4/2017 | Hoffman et al. |

FOREIGN PATENT DOCUMENTS

| | | |
|---|---|---|
| EP | 3 088 083 A1 | 11/2016 |
| JP | 2016165276 | 9/2016 |
| JP | 2016168043 | 9/2016 |
| KR | 10-0840949 B | 6/2008 |
| WO | 2017/112911 | 6/2017 |
| WO | 2017/112911 A1 | 6/2017 |

OTHER PUBLICATIONS

Japanese Office Action dated Apr. 13, 2021.
English Translation of Japanese Office Action.
JP 2016168043 _ English Translation.
JP 2016165276 _ English Translation.
Korean Office Action which issued in counterpart Korean application dated Feb. 25, 2021.
English Translation of Korean Office Action.
KR 10-0840949 B _ English Translation.
European Search Report for Application No. EP 20162792.4-1101 dated May 27, 2020.

*Primary Examiner* — Cynthia B Wilder (74) *Attorney, Agent, or Firm* — Ladas & Parry LLP (57) ABSTRACT

The present invention discloses a Polymerase Chain Reaction (PCR) apparatus for real-time detecting of one or more fluorescent signals. According to the apparatus, the PCR is performed by controlling heating and cooling intervals of a reagent container receiving space. With the aid of an added specific probe and fluorescent material, as well as a light source and a spectrometer, a generated fluorescent signal is detected. Meanwhile, the apparatus is also pre-loaded with an algorithm configured to analyze and quantify the fluorescent signal in a real-time manner.

23 Claims, 7 Drawing Sheets

PCR APPARATUS FOR REAL-TIME DETECTING OF ONE OR MORE FLUORESCENT SIGNALS

BACKGROUND OF THE INVENTION

This application claims the benefit of Republic of China (Taiwan) Patent Application No. 108120548, filed on Jun. 13, 2019, at the Taiwan Intellectual Property Office, the disclosures of which are incorporated herein in their entirety by reference.

1. Field of the Invention

The present invention relates to a Polymerase Chain Reaction (PCR) apparatus, and more particularly to a PCR apparatus for real-time quantifying of one or more fluorescent signals.

2. Description of the Related Art

Polymerase Chain Reaction (PCR) is a technique for rapidly amplifying DNA. The principle and main operation steps are as follows: (a) denaturing: a double-stranded DNA is dissociated into single-stranded DNAs by incubation at 90° C. to 95° C., and then the single-stranded DNAs are used as templates for replication; (b) primer annealing: when the temperature is lowered to an appropriate temperature, a primer will be attached to a correct target gene position; and (c) primer extension: a reaction temperature is corrected to 72° C., and the DNA polymerase successively attaches deoxy-ribonucleotide triphosphate (dNTPs) to the primer to synthesize another strand of a new DNA fragment.

Nucleic acid amplification is repeated continuously through the three steps: denaturing, primer annealing and primer extension. The number of target genes can be doubled in each three-step operation. If the three-step operations are set to be cyclically performed by 40 times, the number of target genes can be amplified by nearly $10^9$ times, and a large number of target gene fragments can be obtained by the PCR in vitro. Therefore, as one of molecular diagnostic techniques widely used in clinical diagnosis at present, the PCR can be applied to items including diagnosis of genetic diseases, diagnosis of pathogenic bacteria, diagnosis and prognosis evaluation of tumors and cancers, basic research and the like, so that the PCR is also used as a technique that is extensively used by the current clinical diagnosis.

In recent years, real-time polymerase chain reaction, also known as quantitative real-time polymerase chain reaction (Q-PCR) (hereinafter referred to as real-time PCR), has been developed in response to technique development requirements. Real-time PCR and traditional PCR both use a thermal cycle step to amplify traced DNAs of the target genes for amplification purposes, one difference being that for real-time PCR, a non-specific fluorescent material or a specific fluorescent probe is added, after each PCR amplification cycle, the DNA of a target gene is amplified and a fluorescent signal is generated simultaneously, and then the fluorescent signal of a product is detected and recorded; after PCR is completed, a graph is drawn according to a cycle number and the fluorescent signals in order to obtain a reaction curve diagram which perfectly shows the product generation of each cycle in PCR; and the reaction curve diagram is analyzed through a built-in program to obtain a real-time quantitative result.

A currently and commonly used non-specific fluorescent dye is SYBR Green I, which binds to a minor groove of a DNA molecule to release fluorescence, so that the number of PCR products generated in each cycle can be obtained by measuring the fluorescence intensity at the end of the primer extension step of each cycle in the PCR process. However, since the SYBR Green I can bind to all double-stranded DNAs, it is impossible to distinguish specific products from non-specific products, so that the SYBR Green I is relatively low in specificity for products, and sometimes false positive results are obtained.

A currently and commonly used specific fluorescent probe is a TaqMan probe, which is a synthetic oligonucleotide with the specificity for a target gene sequence. Different fluorescent materials are labeled respectively at two ends of the oligonucleotide: the molecule at the 5' end is called a reporter and the molecule at the 3' end is called a quencher. If the specific probe is in a free state, the interaction between the reporter and the quencher will quench the fluorescence of each other, so that no fluorescence will be generated. However, when a PCR product is generated, after the specific probe is hydrolyzed, the quencher loses the efficacy in quenching the reporter, so that the fluorescence of the reporter can be detected. Since the specific probe is the oligonucleotide specific only to the target gene, it would not bind to other non-specific products. At present, the commonly used fluorescent dyes in combination with the TaqMan probe include: FAM™ fluorescent dye, VIC® fluorescent dye, HEX™ fluorescent dye, ROX™ fluorescent dye, CY3® fluorescent dye, CY5® fluorescent dye, CY5.5® fluorescent dye, JOE™ fluorescent dye, TET™ fluorescent dye, TEXAS RED® fluorescent dye, TAMRA™ fluorescent dye, NED™ fluorescent dye, Quasar QUASAR®705 fluorescent dye, ALEXA FLUOR®488 fluorescent dye, ALEXA FLUOR®546 fluorescent dye, ALEXA FLUOR®594 fluorescent dye, ALEXA FLUOR®633 fluorescent dye, ALEXA FLUOR643™ fluorescent dye and ALEXA FLUOR®680 fluorescent dye.

Each of these fluorescent dyes has its optimal absorption wavelength range and scattering wavelength range, but most of the optimal absorption wavelength ranges and scattering wavelengths of the above fluorescent dyes are often overlapped, so that when two or more fluorescent dyes are needed to simultaneously quantify two or more different target genes in the same test tube for the same specimen, fluorescent dyes that do not produce a high signal crosstalk will be practically selected and combined for use, and the obtained data is analyzed by a traditional data mode; and distinguishable fluorescent signals are obtained in the end to facilitate the interpretation of the results. The other method is such that only one target gene is tested in one test tube at one time, but there are several test tubes to detect different target genes of the same specimen; and the detection results of several detection targets in the specimen are combined. Through this method, a situation in which the data cannot be analyzed due to the fluorescent signal crosstalk can be avoided. The advantage of the former method is that no matter how many target genes are tested, they can be tested in the same test tube, so that there is less waste of consumables. However, the disadvantage is that there are a plurality of sources of fluorescent signals, which would cause a signal crosstalk phenomenon and results in errors in data analysis, or an inability to effectively distinguish which target gene the signal crosstalk part belongs to, thus it is easy to cause a misjudgment in the experimental results. In the latter method, only one target gene is tested in one test tube, and a plurality of test results are combined for analysis, so that the problem of signal crosstalk can be effectively resolved indeed, and the accuracy of signal identification is much higher than that of the former method However, it may consume many consumables, and a relatively large amount of specimens are needed. At present, when a plurality of target genes needs to be quantified for the same specimen, the latter method is often used.

At present, most of the apparatuses used for real-time PCR in a laboratory often use a temperature-controlled metal as a heater. Heating and cooling operations are repeatedly performed based on the characteristics of rapid heating and cooling of the temperature-controlled metal, so as to reach the reaction temperatures of three steps: denaturing, primer annealing and primer extension. Furthermore, energy is transferred to the reagents and the reactants (including fragments of the target genes) in the test tube by heating the plastic-made reagent container, so as to achieve the efficacy in amplifying signals of target genes and detecting their fluorescent signals. However, such a machine that uses the temperature-controlled metal to repeatedly perform heating and cooling is generally bulky. That is, to obtain effective temperature control, the entire temperature control system must have a relatively large size and heat capacity ratio. Furthermore, according to the design of the current machine, it takes most of the time for the machine to wait for heating or cooling the temperature-controlled metal to the reaction temperature. If the number of cycles required for a regular test is about 30 to 35 cycles, it needs a reaction time of about two to three hours for the conventional machine. As a result, it is difficult to shorten the reaction time. Therefore, such a conventional machine cannot be applied to the test that the result could be obtained within the extremely short period.

In order to alleviate the problems of the conventional apparatus, researchers have applied real-time PCR to a microfluidic wafer technique. This technique has the advantage that a microfluidic wafer can reduce the volume of the reagent or reactant and the entire heat capacity ratio, and the reaction time can thus be shortened and the reagent consumption can be reduced. However, because this technique still needs circulated heating and cooling in three different temperature intervals, there is still a problem of an extremely long heating and cooling time.

Another developed real-time PCR microfluidic wafer lacks the setting of repeated heating and cooling of a heater, and uses a specially designed driving force to pressurize the reactant and the reagent in a flow path, so that the reactant and the reagent repeatedly flow through a specially processed and designed flow path with three different temperature intervals to achieve amplification of the target gene and signal detection. Real-time PCR performed using this technique can eliminate the time consumption caused by heating and cooling, but the system for this technique needs to include a complicated pressurization system and a hydraulic drive system. The hydraulic drive system is also highly related to the volume viscosity of liquid, so that difficulties in the manufacture and control of the system and instrument arise. Accordingly, the development of this technique is indirectly limited.

Researchers have also developed another technique for performing real-time PCR using a thermal convection cycle to solve the problems of high capacitance ratio and high time consumption in conventional machines. This technique uses two heat sources with different temperatures to heat the upper and lower ends of a closed test tube which contains the reagent and the reactant. The reagent and the reactant are driven by the temperature difference between the upper and lower ends to flow through the different temperature intervals of the test tube, so as to perform real-time PCR. This technique overcomes the time consumption caused by the repeated heating and cooling of the heater, and does not need to drive the hydraulic circulation in the test tube by external pressurization. However, because the heater is usually a piece of metal and its heat capacity ratio cannot be reduced, the size of the machine cannot be minimized. Furthermore, the complicated temperature control mechanism and the metal heating system also results in the high manufacturing cost of the machine.

When multiple target genes or objects need to be quantified for the same specimen, the above problems on the combination of fluorescent probes and the machine would be more serious. That is, in order to obtain a highly reliable fluorescent signal value, one target gene would be merely used in one test tube for one time in practice, and a plurality of test results are combined for determination. If doing so, the test for each specimen needs to use a plurality of test tubes. If the machine is one that is usually used in a laboratory, or if the microfluidic wafer is repeatedly heated and cooled at different temperature intervals, there still has problems on the consumption of consumables and the requirement for more specimens in addition to the issue of the longer test time. Even if the test is performed on the microfluidic wafer with the special flow path design or on the apparatus for the real-time PCR test using the thermal cycle, and the problem of the longer test time can be eliminated, the issues of the consumption of consumables and the requirement for more specimens still cannot be overcome.

In view of the above problems, the present invention discloses a PCR apparatus which can overcome the problems of oversized dimension and time consumption caused by repeated heating and cooling in the conventional machine and can simultaneously overcome the problems of the consumption of consumables and the requirement for more specimens.

SUMMARY OF THE INVENTION

The present invention relates to a Polymerase Chain Reaction (PCR) apparatus for real-time detecting of one or more fluorescent signals. The apparatus includes a reagent container holding mechanism (or component) which is formed by a heat-resistant material. The surface layer of the heat-resistant material may include a heat-resistant insulating material or a conductive thin film, which is formed by coating with conductive material, or both the heat-resistant insulating material and the conductive thin film. Furthermore, the reagent container holding mechanism may have different structural designs according to different external contours of reagent containers and different temperature control conditions; and other conductive components such as a circuit board or conductive metal component may be also incorporated to facilitate the operation. The heat-resistant material may be metal or non-metal. If it is metal, the heat-resistant material may be aluminum, copper, the alloy thereof or other heat-resistant metals. If it is non-metal, the heat-resistant material may be glass, plastic, or ceramic. If the heat-resistant material is metal, the metal may be coated with a layer of heat-resistant insulating material, such as aluminum oxide, polytetrafluoroethylene or polyimide.

Regardless of the heat-resistant material being a metal or not, the surface of the heat-resistant material would be coated with a conductive thin film to provide a specific resistance value, which depends on the design of heating mechanism of the reagent container holding mechanism. If the design of the heating mechanism only includes a metal-made conductive material without other heating components, the surface layer of the heat-resistant material of the apparatus disclosed by the present invention would be coated with a conductive thin film. Because the conductive thin film has specific resistance value, the heating mechanism starts to heat when receiving current. On the contrary, if the heating mechanism is designed to include an electric heating apparatus, such as a circuit board with an electric heating element welded thereon, the reagent container holding mechanism can be started to heat after being electrified, and thus the heat-resistant material no longer needs to be coated with a layer of conductive thin film. The conductive material of the present invention may be: tin oxide, indium oxide, zinc oxide, indium tin oxide, chromium, titanium, tantalum or copper. The electric heating element of the present invention may be a resistor or a printed circuit board (PCB) layout. According to the design of heating mechanism disclosed by the present invention, the size of the heating mechanism may be greatly reduced. Compared with a traditional PCR machine, the apparatus has more advantages in size and derivativeness.

The portion, in contact with the reagent container, of the reagent container holding mechanism is provided with at least one temperature sensor. The position and the number of temperature sensors may depend on the position of the reagent container disposing in the reagent container holding mechanism, at which temperature change can be easily detected and the reaction in the reagent container would not be affected. The temperature sensor is configured to monitor and report the temperature at the position.

The present invention also includes a power supply, a heat dissipation apparatus and a processor. The power supply is configured to supply power for heating and cooling of the reagent container holding mechanism and the operation of whole apparatus. The heat dissipation apparatus is configured to cool the system. The processor is pre-loaded with a program, so as to quantify and analyze one or more fluorescent signals by using an algorithm. The algorithm may be one in which the parameters are set based on the least square method.

In addition to the analysis of the fluorescent signals, the processor may be further configured to: control the time points to start the power supply to heat the reagent container holding mechanism, to start the heat dissipation apparatus, and to turn on and/or off the light source of the system. The power supply is electrically connected to the reagent container holding mechanism. More precisely, the connector of the power supply may be electrically connected to the conductive thin film on the surface layer of the reagent container holding mechanism, or electrically connected to other electric heating element of the reagent container holding mechanism. When the power supply starts to supply the power, the reagent container holding mechanism begins being heated to a predetermined temperature, and in this case, the temperature sensor arranged in the reagent container holding mechanism would start to detect the temperature and report the temperature to the processor. When the temperature sensor detects that the temperature of the reagent container holding mechanism meets the highest temperature predetermined by the system for a predetermined period of time, the heat dissipation apparatus is started to cool the reagent container holding mechanism to a low temperature interval predetermined by the system. The installation position of the heat dissipation apparatus or the position of the heat dissipation apparatus relative to the reagent container holding mechanism is not specifically defined, as long as the temperature of the apparatus may be rapidly and effectively lowered. In the temperature setting of the present invention, the heating temperature interval of the reagent container holding mechanism may be allowed to be 85° C. to 130° C., and the cooling temperature interval of the reagent container holding mechanism may be allowed to be 50° C. to 75° C.

In one preferred embodiment of the present invention, the heat dissipation apparatus may be a fan. Furthermore, a thermoelectric (TE) cooler or one or more fans may be incorporated with the heat dissipation apparatus to achieve rapid and effective cooling. The heat-resistant material constituting the reagent container holding mechanism may also include a plurality of heat dissipation holes penetrating therethrough, so as to accelerate heat dissipation.

The apparatus disclosed by the present invention is provided with at least one light source, at least one spectrometer. The light source is configured to excite a fluorescent dye or a fluorescent probe to generate detectable fluorescence. The apparatus disclosed by the present invention also may be incorporated with a plurality of light sources having different wavelengths for excitation. The beam emitted from the light source may enter into the reagent container at a specific angle through a light illumination lens, and excites the fluorescent material to generate the fluorescence. The generated fluorescence passes through a fluorescence outlet and a light detection lens and then enters into the spectrometer. The spectrometer processes the fluorescence into the fluorescent signal in spectrum format and then the signal is sent to the processor for analysis. The light source adopted in the present invention includes a light emitting diode (LED), a laser, or other light sources having wavelengths being consistent with the absorption wavelengths of the fluorescent dyes or fluorescent probes, and these light sources also may be incorporated for use. The light illumination lens and the light detection lens adopted in the present invention may be: biconvex lenses, piano-convex lenses, doublet lenses, aspheric lenses, achromatic lenses, anastigmatic lenses, Fresnel lenses, piano-concave lenses, biconcave lenses, positive/negative meniscus lenses, axicons, gradient index lenses, micro-lens arrays, cylindrical lenses, waveguide elements, diffractive optical elements, holographic optical elements, or a combination thereof. The processor can control the time to turn on and turn off the light source, and also can control whether the spectrometer starts to detect the fluorescent signal upon the light source is turned on.

There is no specifically defined arrangement for the light source, the spectrometer, the light illumination lens, the light detection lens or the reagent container holding mechanism in the apparatus of the present invention, as long as the arrangement basically ensures that the light source (and the light emitting path thereof) and the light illumination lens are located at one side of the reagent container holding mechanism, and the beam emitted from the light source can pass through the light illumination lens and can be guided into the reagent container to effectively excite the fluorescent dye or fluorescent probe of the reagent. In addition, the generated fluorescence can be transmitted to the spectrometer through the light detection lens, followed by transmitting the fluorescent signal in spectrum format, which is processed by the spectrometer, into the processor for relevant signal analysis. In one preferred embodiment of the present invention, the light source and the light illumination lens are located under the reagent container holding mechanism, and the light detection lens and the spectrometer are arranged to form a fictitious line, which is perpendicular to the other fictitious line formed by the light source and the light illumination lens. In another preferred embodiment disclosed by the present invention, the reagent container holding mechanism may be provided with a fluorescence outlet on a fluorescence emitting path, so as to facilitate the operation of the apparatus disclosed by the present invention.

According to the apparatus disclosed by the present invention, the detectable fluorescent signal for the spectrometer is ranged from 340 nm to 850 nm. The emission wavelength of the fluorescent dye or fluorescent probe used in the present invention should also range from 340 nm to 850 nm, and the fluorescent dye includes, but is not limited to: FAM™ fluorescent dye, VIC® fluorescent dye, HEX™ fluorescent dye, ROX™ fluorescent dye, CY3® fluorescent dye, CY5® fluorescent dye, CY5.5® fluorescent dye, JOE™ fluorescent dye, TET™ fluorescent dye, SYBR® fluorescent dye, TEXAS RED® fluorescent dye, TAMRA™ fluorescent dye, NED™ fluorescent dye, QUASAR705®, ALEXA FLUOR®488, ALEXA FLUOR®545, ALEXA FLUOR®594, ALEXA FLUOR®633, ALEXA FLUOR643™ and ALEXA FLUOR®680. Other fluorescent dyes having emission wavelengths between 340 nm and 850 nm also may be applied in the present invention.

The apparatus disclosed by the present invention may detect a plurality of target genes or objects in the same reagent container. That is, one or more fluorescent dyes or fluorescent probes are added to the same reagent container to perform the real-time PCR, and the fluorescent signals for each reaction are collected. The fluorescent signals are analyzed by the algorithm pre-loaded in the processor to achieve the qualitative and quantitative results for the plurality of target genes or objects. When one or more fluorescent dyes or fluorescent probes are added, signal crosstalk may occur between the fluorescent signals. In order to effectively detect and identify two or more fluorescent signals in the same reagent container in a real-time manner, firstly, a standard fluorescence spectrum of the fluorescent dye or fluorescent probe to be used is input into the algorithm which is pre-loaded in the processor, a standard spectrum of the excitation light source used by the apparatus is also input into the processor, and two spectrums are used as the standard values of the algorithm Subsequently, a measured original fluorescent signal and the standard spectrum are calculated and compared through the algorithm to obtain a fluorescent signal value proportional to the concentration of the target genes. For example, if six different target genes or objects are to be detected in the same reagent container (i.e., six different fluorescent dyes or fluorescent probes need to be used), the standard spectrums of the six fluorescent dyes or fluorescent probes should be input into the algorithm which is pre-loaded in the processor, and the standard spectrum of the excitation light source is also input into the algorithm which is pre-loaded in the processor, followed by performing the real-time PCR. After completing the operation of the program, the processor may receive the measured original spectrum data, and the original data are the superimposed fluorescent signal of six fluorescent dyes or fluorescent probes. After the background value is deducted, the individual duty ratios of six fluorescent signals in the fluorescent spectrums of each PCR cycle are calculated using the algorithm. Real-time fluorescent signal values of the individual fluorescent dyes or fluorescent probes can be separated and obtained through the calculation. After conversion, qualitative and quantitative results of six different target genes or objects can be obtained.

During the operation of the apparatus disclosed by the present invention, the power supply is turned on at first, and the conductive material is then started to be electrified to warm up the reagent container holding mechanism. The reagent container containing the reactant and the reagent is disposed into the holding space of the reagent container holding mechanism. Through rapid and repeated heating and cooling on the reagent container holding mechanism, the reactant and the reagent start to undergo denaturing steps, primer annealing steps, primer extension steps. At specific moment, the processor turns on a light source switch, and the emitted excitation light enters into the reagent container through the light illumination lens and excites the fluorescent material in the container to emit fluorescence. The generated fluorescence passes through the light detection lens and is received and processed into fluorescent signal in spectrum format by the spectrometer. The signal is transmitted to the processor for signal analysis. Finally, qualitative or quantitative analysis may be performed for the target gene or object to be detected in the reagent container.

According to the apparatus disclosed by the present invention, the conductive thin film or electric heating element is incorporated with the small-sized heating mechanism to provide the rapid heating and cooling functions, so that the time for PCR is effectively shortened. Meanwhile, the fluorescence values of one or more fluorescent signals may be analyzed in a real-time manner through the built-in algorithm, so as to qualitatively and quantitatively determine the target genes within a short time. In order to fulfill the foregoing purpose, the preferred embodiment according to the present invention is provided as follows.

BRIEF DESCRIPTION OF THE DRAWINGS

FIGS. 2-1 and 2-2 are schematic diagrams showing a reagent container holding mechanism, a heat dissipation hole and a temperature sensor in the preferred embodiment of the present invention;

FIG. 2-3 is a top view of the reagent container holding mechanism in the preferred embodiment of the present invention;

FIG. 2-4 is a side view of the reagent container holding mechanism in the preferred embodiment of the present invention;

FIG. 2-5 is a top view of the layers of the first and the second substrate in the preferred embodiment of the present invention;

FIG. 5-1 is a schematic diagram showing a reagent container holding mechanism in another preferred embodiment of the present invention;

FIG. 5-2 is a top view of the reagent container holding mechanism in another preferred embodiment of the present invention;

FIG. 6-1 is a schematic diagram showing a reagent container holding mechanism in another preferred embodiment of the present invention; and FIG. 6-2 is a schematic diagram showing a reagent container holding mechanism in another preferred embodiment of the present invention.

PREFERRED EMBODIMENT OF THE PRESENT INVENTION

The structure and function of one preferred embodiment of the present invention will be described in detail below with reference to the accompanying drawings. In addition, in this description, the position of a mechanism or positions of its parts are described as "before," "after," "left," "right," "above," "below," etc., which correspond to the spatial relationship when a user operates the present preferred embodiment.

Figure 1:
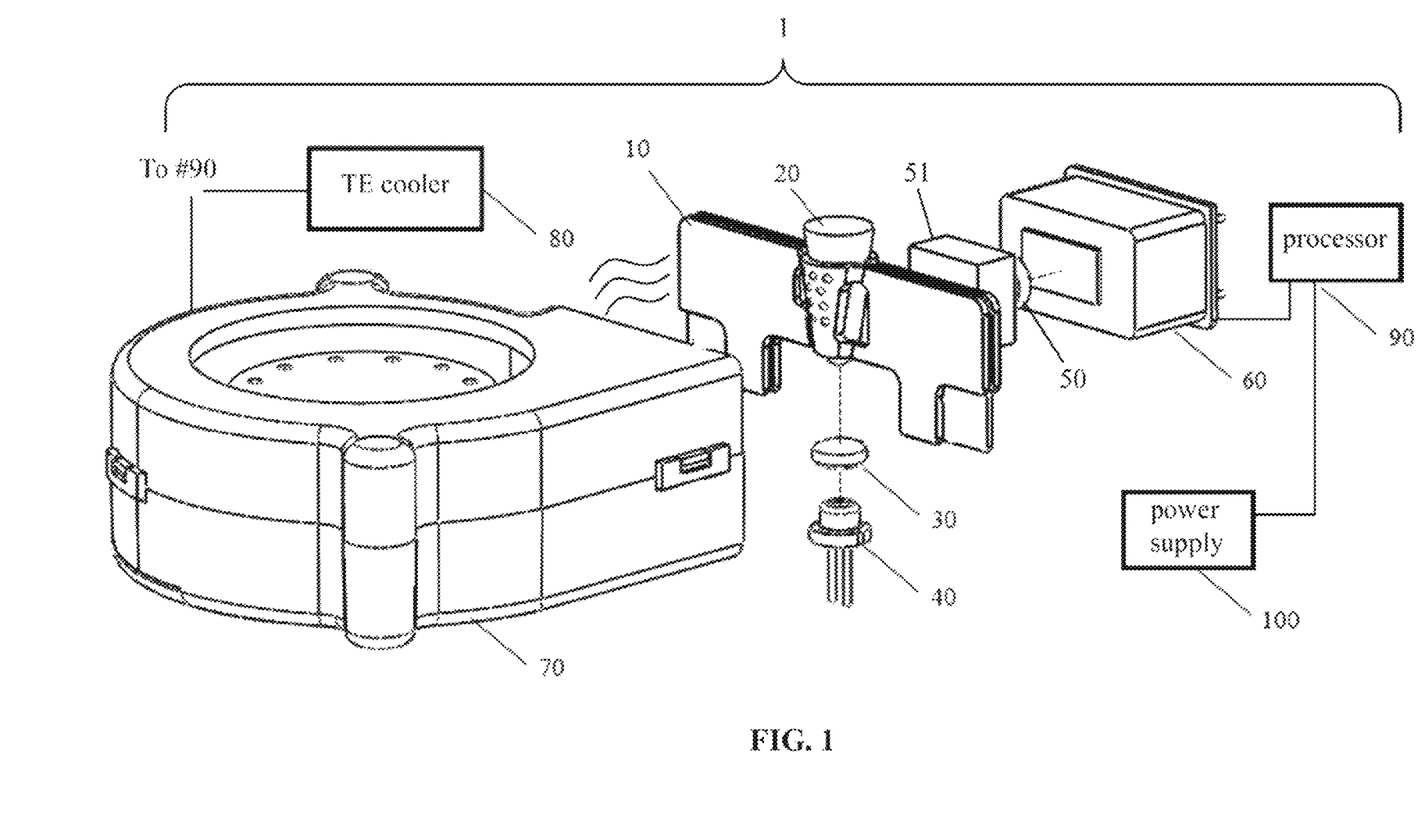
FIG. 1 is a schematic diagram showing the component configuration of an apparatus in one preferred embodiment of the present invention.
Figure 23:
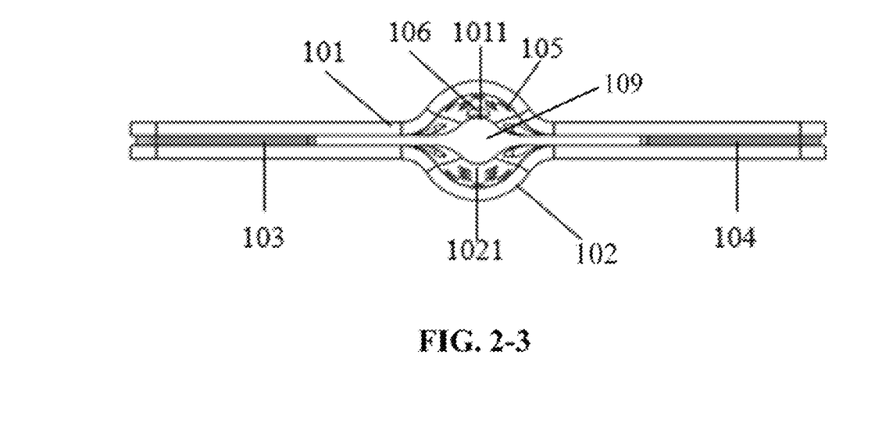
Figure 24:
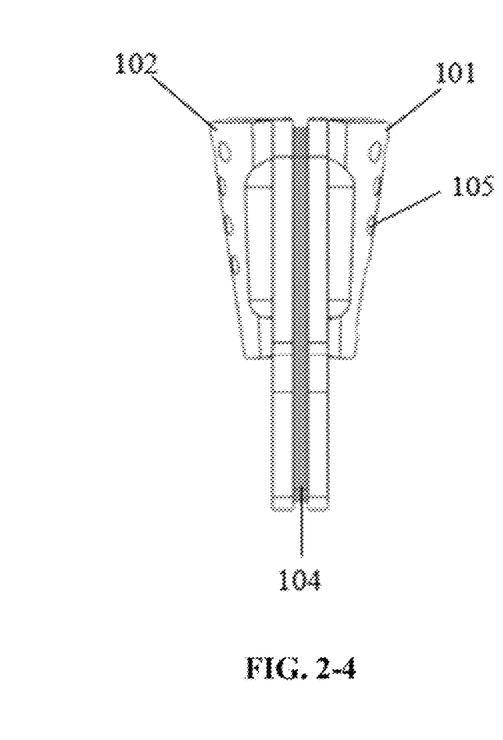
Figure 25:
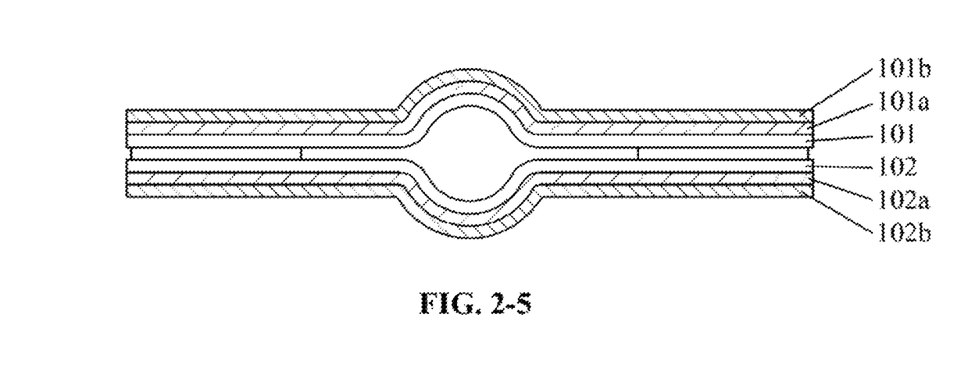

Please refer to FIG. 1, which shows the component configuration for constituting an apparatus (1) in one preferred embodiment of the present invention. The apparatus (1) in the preferred embodiment of the present invention includes a reagent container holding mechanism (10), a first optical element (30), a light source (40), a second optical element (50), a spectrometer (60), a fan (70), a thermoelectric cooler (80), a processor (90) and a power supply (100). The reagent container holding mechanism (10) is configured to deposit a reagent container (20) and provide a space (109, referring to FIG. 2-3) for heating the reagent and the reactant, and the power supply (100) is electrically connected to the reagent container holding mechanism (10). The fan (70) and the thermoelectric cooler (80) are configured to electrically connect to the power supply (100) to cool the reagent container holding mechanism (10). In addition, the first and the second optical elements (30, 50) include but is not limited to biconvex lens, piano-convex lens, doublet lens, aspheric lens, achromatic lens, anastigmatic lens, Fresnel lens, plano-concave lens, biconcave lens, positive/negative meniscus lens, axicon, gradient index lens, microlens array, cylindrical lens, diffractive optical element, waveguide element, holographic optical element, mirror, fiber and prism.

Please refer to FIGS. 2-1 to 2-5, which show the reagent container holding mechanism (10) in the preferred embodiment of the present invention. The reagent containing holding mechanism (10) includes a first substrate (101) having a first concave surface (1011), a second substrate (102) having a second concave surface (1021), a first metal sheet (103), and a second metal sheet (104). The first substrate (101) has a first heat dissipation hole (105) and a second heat dissipation hole (107) for the purpose of heat dissipation, and the first substrate (101) also has a first fluorescence outlet (106) and a first temperature sensor (108). The first temperature sensor (108) is configured to detect the temperature of the reagent container holding mechanism (10) and report the temperature to the processor (90). The second substrate (102) only has a first heat dissipation hole (105) and a second heat dissipation hole (107).

The first substrate (101) and the second substrate (102) are in mutually parallel arrangement so that the first concave surface (1011) and the second concave surface (1021) are mutually coupled in a mode of being perpendicular to a horizontal plane, and form a space (109) for placement of the reagent container (20). The outer wall of the reagent container (20) is in thermal contact with the first concave surface (1011) and the second concave surface (1021). There is no special limit to the contours of the first concave surface (1011) and the second concave surface (1021), as long as the contours may substantially be consistent with the reagent container (20). In the present embodiment, since the reagent container (20) is a test tube, the contour of the space (109) formed by facing the first concave surface (1011) to the second concave surface (1021) for placement of the reagent container (20) is the contour of the exterior surface of the test tube. The first metal sheet (103) and the second metal sheet (104) are sandwiched between the first substrate (101) and the second substrate (102), and are parallel to the first substrate (101) and the second substrate (102). Furthermore, the first metal sheet (103) and the second metal sheet (104) are located at two ends of the first substrate (101) and the second substrate (102). The first metal sheet (103) and the second metal sheet (104) are connected to the power supply (100).

In the present embodiment, the base material of the first substrate (101) and the second substrate (102) is aluminum. The base material is firstly anodized, and plated with a layer of aluminum oxide followed by plating with a layer of the conductive thin film. The material of the conductive thin film of the present embodiment may be: tin oxide, indium oxide, zinc oxide, indium tin oxide, chromium, titanium, tantalum or copper. The material of the first metal sheet (103) and the second metal sheet (104) is copper in the present embodiment.

Please refer to FIG. 1, in the present embodiment, the light source (40) is a laser diode, which is configured to excite fluorescent dyes or fluorescent probes to generate detectable fluorescence. If needed, the light source (40) may also be replaced with a set of laser lights or a LED. The first optical element (30) is configured to guide the beam emitted from the light source (40) to the reagent container (20). In the present embodiment, the reagent container (20) has been already placed in the reagent container holding mechanism (10). The light source (40) and the first optical element (30) are located under the reagent container (20) and are arranged vertically together with the reagent container (20). Furthermore, the first optical element (30) is located between the light source (40) and the reagent container (20). Such an arrangement ensures that the excitation light emitted from the light source (40) is guided by the first optical element (30) to the bottom of the reagent container (20), so as to excite the fluorescent dye or fluorescent probe in the reagent container (20).

Please refer to FIG. 1, in the present embodiment, the second optical element (50) is configured to transmit the generated fluorescence to the spectrometer (60). The second optical element (50) can include an optical filter (51) located between the reagent container holding mechanism (10) and the spectrometer (60), and the optical filter (51) is configured to filter out the light exceeding the wavelength range of the one or more fluorescent signals. The spectrometer (60) process the fluorescence into the fluorescent signal in spectrum format, and then transmits the signal to the processor (90) for signal analysis. The second optical element (50) and the spectrometer (60) are located at the side, which is closed to the first substrate (101) of the reagent container holding mechanism (10), and the second optical element (50), the spectrometer (60), and the first fluorescence outlet (106) need to be horizontally arranged as much as possible, so that the excited fluorescent signal in the reagent container (20) may sequentially pass through the first fluorescence outlet (106) and the second optical element (50), whereupon it is emitted straightly and detected by the spectrometer (60). In the present embodiment, the second optical element (50) and the spectrometer (60) are located at one side of the reagent container holding mechanism (10), and a fictitious line formed by the arrangement of the second optical element (50) and the spectrometer (60), and the other fictitious line formed by the arrangement of the first optical element (30) and the light source (40) are perpendicular.

Please refer to FIG. 1, in the present embodiment, the fan (70) is a heat dissipation apparatus, is used to incorporated with the thermoelectric cooler (80), and the position of the fan (70) is not specified. In the present embodiment, the fan (70) is located at the side, which is closed to the second substrate (102) of the reagent container holding mechanism (10), and the thermoelectric cooler (80) is located above the fan (70). When the apparatus (1) starts to be cooled, the first heat dissipation hole (105) and the second heat dissipation hole (107) will dissipate heat synergistically. The apparatus (1) of the present embodiment includes a processor (90), and the least square method-based algorithm for fluorescent signal analysis is pre-loaded in the processor (90). In the present embodiment, a standard spectrum of the fluorescent dye or fluorescent probe to be used and a spectrum of the light source (40) should be input for the purpose of subsequent data analysis.

The processor (90) also receives the signal of the first temperature sensor (108). When the temperature of the reagent container holding mechanism (10) exceeds the temperature range set by the system, the fan (70) and the thermoelectric cooler (80) are turned on to cool the reagent container holding mechanism (10). When the temperature of the reagent container holding mechanism (10) is lower than the temperature range set by the system, the power supply (100) starts to heat the apparatus (1). In the present embodiment, in order to be consistent with heating rate control, the processor (90) may further control the first metal sheet (103) and the second metal sheet (104) to be simultaneously electrified and heated, or control only the first metal sheet (103) or the second metal sheet (104) to be heated.

The present embodiment also includes a power supply (100), which is configured to provide power required by the entire apparatus (1). When the power supply (100) is turned on, current is transmitted to the first metal sheet (103) and the second metal sheet (104). Because the material of the first metal sheet (103) and the second metal sheet (104) is copper, the current can be conducted to the portions of the first substrate (101) and the second substrate (102) in contact with the first metal sheet (103) and the second metal sheet (104). Because the surface layers (101a, 102a) of the first substrate (101) and the second substrate (102) are coated with conductive thin films (101b, 102b) having specific resistance values, the reagent container holding mechanism (10) starts to be heated to a temperature interval of 95° C. to 100° C. which is a heating temperature interval set in the present embodiment. Furthermore, in the present embodiment, the processor (90) is programmed so that the reagent container holding mechanism (10) may be maintained within this heating temperature interval for about 6 s to 15 s to perform the step of the real-time PCR in the reagent container (20). Subsequently, the processor (90) may be programmed to start the fan (70) and/or the thermoelectric cooler (80) to start cooling the reagent container holding mechanism (10) to a temperature interval of 60° C. to 62° C., which is a low temperature interval set in the present embodiment. In the present embodiment, the processor (90) is programmed so that the reagent container holding mechanism (10) may be maintained within this low temperature interval for about 1 s to 5 s to perform the step of the real-time PCR in the reagent container (20). In order to provide effective and sufficient reaction time and temperature, the processor (90) also controls the temperature of the reagent container holding mechanism (10) to be in the repeated cycles of the heating temperature interval and the low temperature interval until the reaction is ended. When the temperature of the reagent container holding mechanism (10) stably increases and decreases in this manner, the temperatures of the reactant and the reagent in the reagent container (20) can reach three temperature intervals required in real-time PCR.

When real-time PCR is started, the reagent and the reactant, neighboring to the reagent container (20) and the reagent container holding mechanism (10), are heated at first. When the reactant and the reagent close to the reagent container (20) are heated to 95° C., the reactant and the reagent at this portion start to process a denaturing step, and reach to the temperatures for primer annealing and primer extension by controlling the temperature cycling of the reagent container holding mechanism (10).

The processor (90) then turns on the switch of the light source (40), and the emitted excitation light enters into the reagent container (20) through the first optical element (30) to excite the fluorescent material in the reagent container (20) to emit fluorescence. The generated fluorescence passes through the second optical element (50), and the spectrometer (60) processed it into the original fluorescent signal. The original fluorescent signal is then transmitted to the processor (90). After processing by the least-square-method-based algorithm which is pre-loaded in the processor and removing the signal values of background light, the data and the pre-input standard spectrum of the fluorescent dye or fluorescent probe are subjected to verification analysis. Finally, the intensity of each fluorescent signals can be obtained, and the qualitative or quantitative analysis may be performed for the target gene or object to be detected in the reagent container (20) via conversion.

Figure 3:
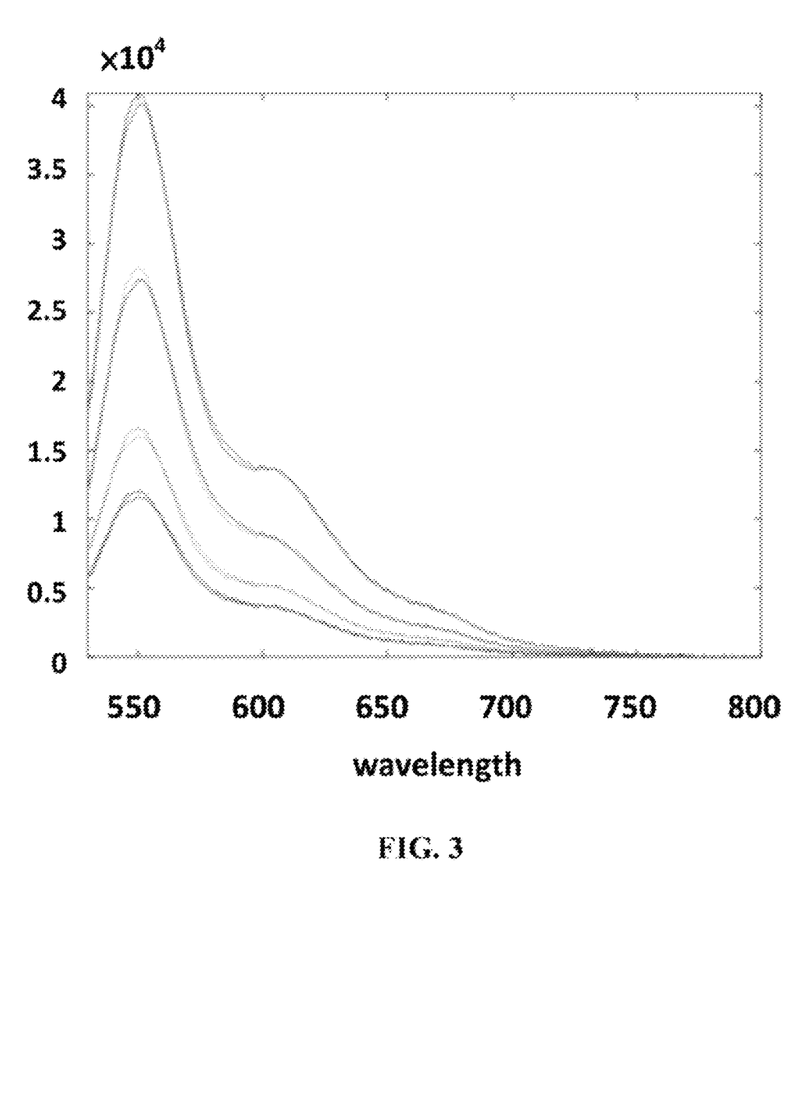
FIG. 3 is a diagram showing the original fluorescent signals in the preferred embodiment of the present invention.
Figure 4:
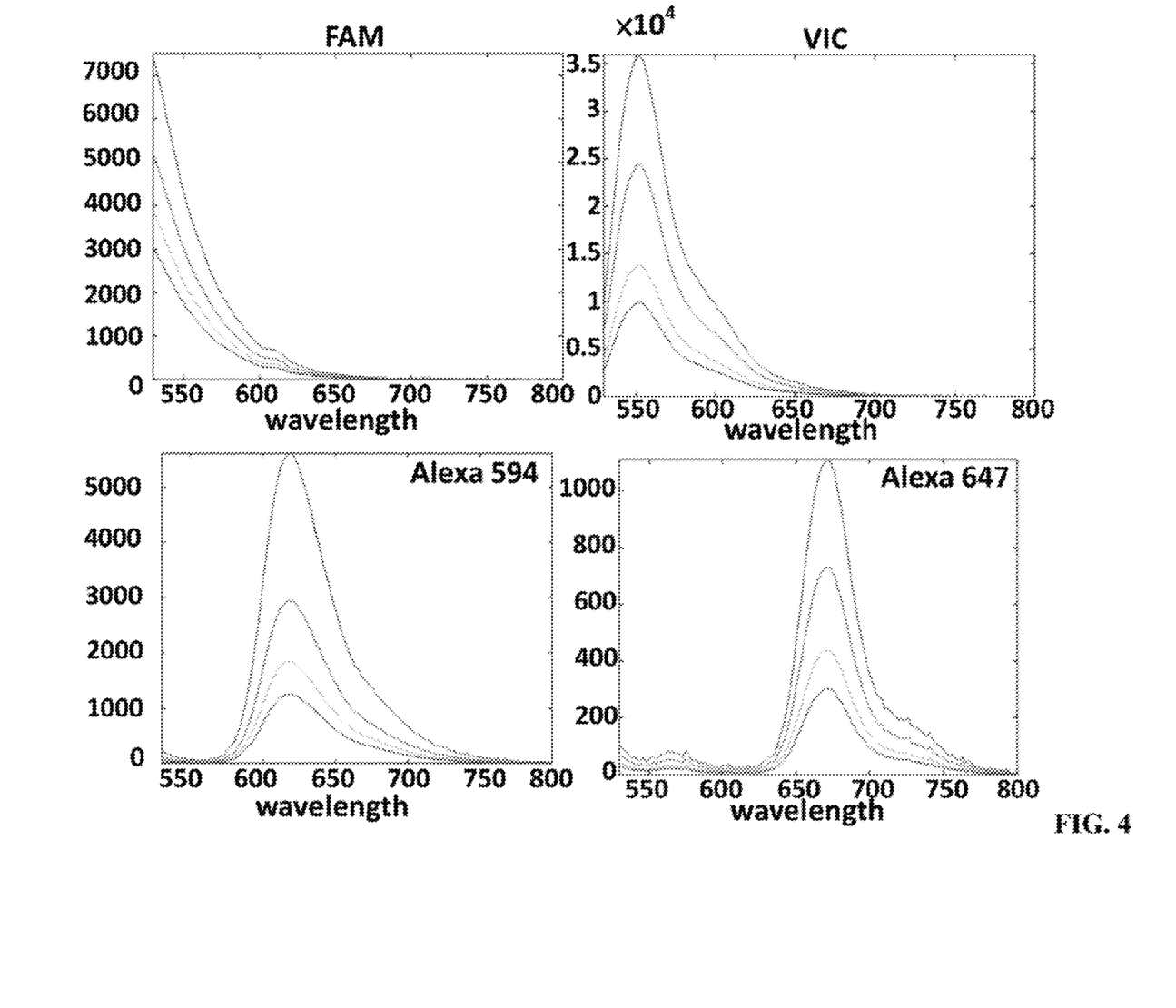
FIG. 4 is a diagram showing the analytic result for the fluorescent signals in the preferred embodiment of the present invention.
Figure 21:
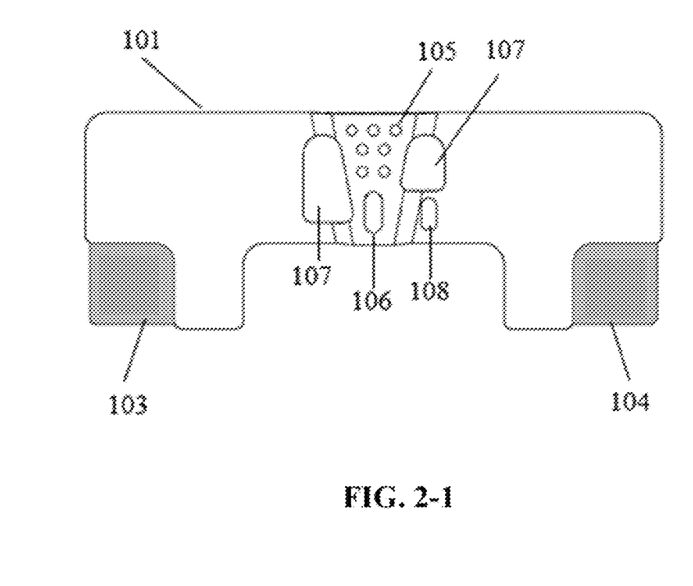
Figure 22:
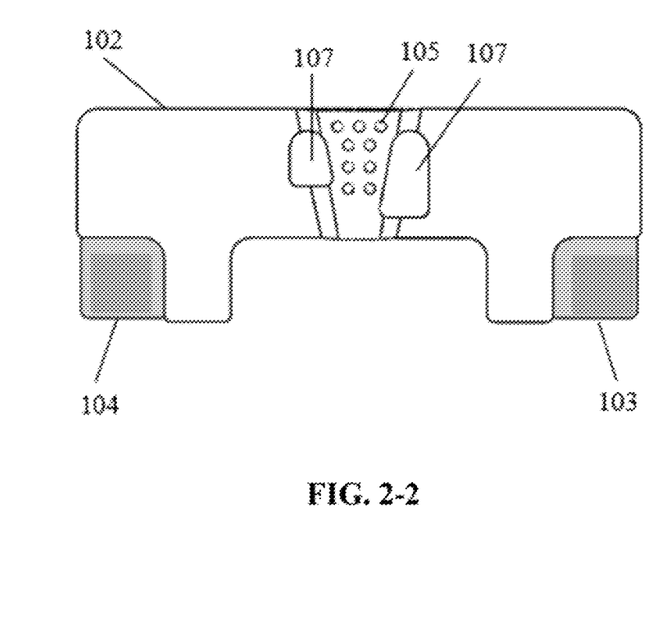

Through the settings in the present embodiment, if four fluorescent probes at different concentrations are respectively added to four reagent containers (20), and each reagent container (20) contains four fluorescent probes FAM™ fluorescent dye, VIC® fluorescent dye, ALEXA FLUOR®594 and ALEXA FLUOR®647 at the same concentration, the mixed original fluorescent data from four reagent containers (20) can be obtained through the implementation of the apparatus (1) at first (as shown in FIG. 3). Subsequently, through the built-in least-square-method-based algorithm; the concentration of each fluorescent probe in four reagent containers (20) may be obtained by analysis (as shown in FIG. 4).

Figure 51:
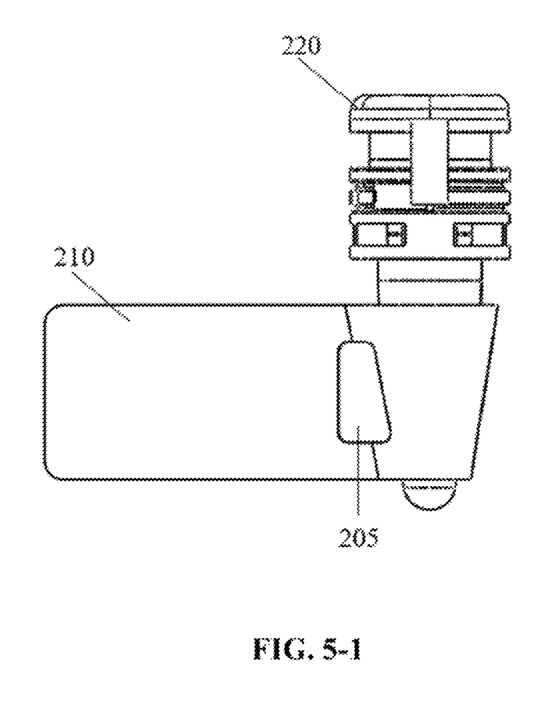
Figure 52:
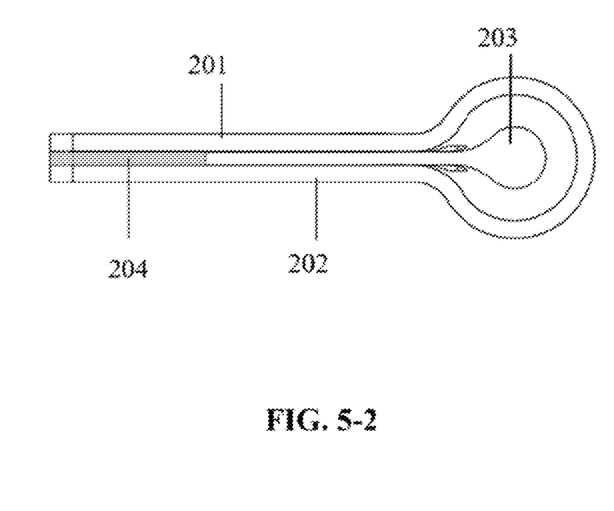

Referring to FIGS. 5-1 and 5-2, in another preferred embodiment, another reagent container holding mechanism (210) can be used to replace the above reagent container holding mechanism (10), and other configurations of the apparatus are the same as those in the previous embodiment. The reagent container holding mechanism (210) includes a third substrate (201), a fourth substrate (202) and an insulating sheet (204). The third substrate (201) has a temperature sensor (205) which is configured thereon to detect the temperature of the reagent container holding mechanism (210) and report the temperature to the processor (90). The third substrate (201) and the fourth substrate (202) are made of the same heat-resistant substrate, which is only bent at specific angles and symmetrically arranged, and the bent portion forms a reagent container receiving place (203). The contour of the reagent container receiving place (203) is not particularly limited, as long as the contour may accommodate the reagent container (220). In the present embodiment, because the reagent container (220) is a test tube, the contour of the reagent container holding place (203) is the same as that of the exterior surface of the reagent container (220). The insulating sheet (204) is included between the third substrate (201) and the fourth substrate (202), and the third substrate (201) and the fourth substrate (202) are respectively connected to the power supply (100).

En the present embodiment, the base material of the third substrate (201) and the fourth substrate (202) is aluminum. The base material is anodized and plated with a layer of aluminum oxide, followed by plating a layer of conductive thin film. The material of the conductive thin film elected for the present embodiment may be: tin oxide, indium oxide, zinc oxide, indium tin oxide, chromium, titanium, tantalum or copper. The power supply (100) is electrically connected to the third substrate (201) and the fourth substrate (202). The third substrate (201) and the fourth substrate (202) are respectively an anode and a cathode, which are separated by the insulating sheet (204), to ensure they are unable to be in contact.

Figures 61, 62:
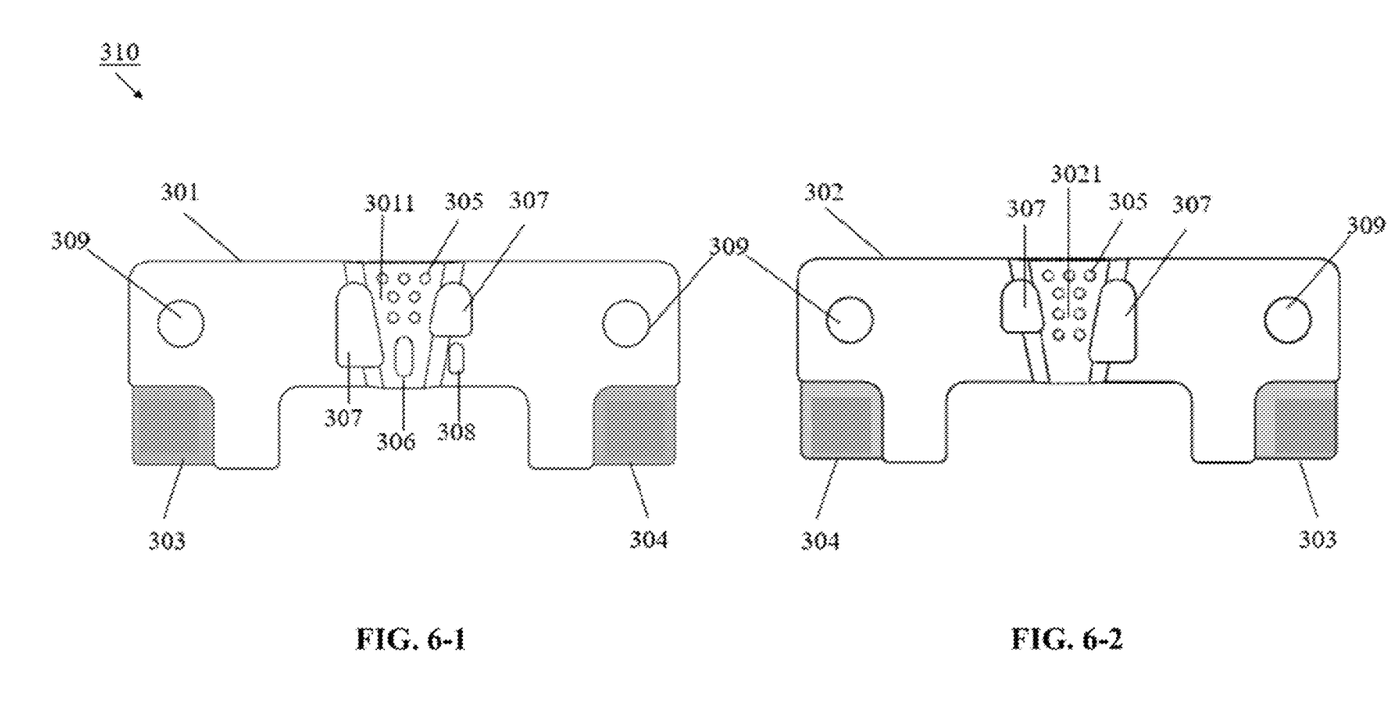

Referring to FIGS. 6-1 and 6-2, in another preferred embodiment, another reagent container holding mechanism (310) may also be used to replace the above reagent container holding mechanism (10), and other components and configurations of the apparatus (1) are the same as those in the aforementioned embodiment. The reagent container holding mechanism (310) includes a fifth substrate (301) having a third concave surface (3011), a sixth substrate (302) having a fourth concave surface (3021), a first circuit board (303) and a second circuit board (304). The fifth substrate (301) has a third heat dissipation hole (305) and a fourth heat dissipation hole (307) thereon for heat dissipation. The fifth substrate (301) also has a second fluorescence outlet (306) and a second temperature sensor (308). The second temperature sensor (308) is configured to detect the temperature of the reagent container holding mechanism (310) and report the temperature to the processor (90). The sixth substrate (302) only has a third heat dissipation hole (305) and a fourth heat dissipation hole (307).

The fifth substrate (301) and the sixth substrate (302) are arranged mutually in parallel to cause the third concave surface (3011) and the fourth concave surface (3021) to be mutually coupled in a mode of being perpendicular to a horizontal plane and form a space for placement of the reagent container (20). The outer wall of the reagent container (20) (not shown in FIGS. 6-1 and 6-2) is in thermal contact with the third concave surface (3011) and the fourth concave surface (3021). The contours of the third concave surface (3011) and the fourth concave surface (3021) are not particularly limited, as long as the contours are consistent with the contour of the reagent container (20). In the present embodiment, because the reagent container (20) is a test tube, the surrounding wall of the space formed by coupling the third concave surface (3011) to the fourth concave surface (3021) for placement of the reagent container (20) is the contour of the exterior surface of the test tube. The first circuit board (303) and the second circuit board (304) are sandwiched within and are parallel to the fifth substrate (301) and the sixth substrate (302). Furthermore, the first circuit board (303) and the second circuit board (304) are respectively located at two opposite ends of the fifth substrate (301) and the sixth substrate (302). The front and rear surfaces of each of the first circuit board (303) and the second circuit board (304) are respectively welded with a resistor (309), and the first circuit board (303) and the second circuit board (304) are jointed with the fifth substrate (301) and the sixth substrate (302). The first circuit board (303) and the second circuit board (304) are also connected to the power supply (100). In the present embodiment, the base material of the fifth substrate (301) and the sixth substrate (302) is aluminum. The base material is anodized and plated with a layer of aluminum oxide.

When the power supply (100) is turned on, current is transmitted to the first circuit board (303) and the second circuit board (304). At this moment, the resistor (309) is electrified and the temperature thereof starts to increase, and drives the temperature of the fifth substrate (301) and the sixth substrate (302) to increase accordingly. Therefore, when the temperature of the reagent container holding mechanism (310) increases to a temperature interval of 95° C. to 100° C., real-time PCR is started. The second temperature sensor (308) detects the temperature of the reagent container holding mechanism (310) and reports the temperature to the processor (90). When the temperature exceeds a heating temperature interval set by the system, the third heat dissipation hole (305) and the fourth heat dissipation hole (307) would facilitate the cooling effect by the fan (70) and the thermoelectric cooler (80). After a fluorescent signal is generated by real-time PCR, the fluorescence emits through the fluorescence outlet (306) and the second optical element (50), and is detected by the spectrometer (60).

What is claimed is:

1. A Polymerase Chain Reaction (PCR) apparatus for real-time detecting and quantifying one or more fluorescent signals in a reagent container, wherein the reagent container is configured to contain a reactant and a reagent containing one or more fluorescent probes or fluorescent dyes, the PCR apparatus comprising:
   a reagent container holding mechanism configured to accommodate the reagent container; wherein the reagent container holding mechanism is formed by:
   (i) a first substrate having a first concave surface, a second substrate having a second concave surface, a first conductive component and a second conductive component, the first and the second conductive components are disposed at two opposite ends of the first substrate and sandwiched between the first and the second substrates, and the first concave surface is faced to the second concave surfaces to form a space to accommodate the reagent container; or
   (ii) a third substrate, a fourth substrate and an electrical insulating material, the third and the fourth substrates are formed of a heat resistant material and bent into a specific shape, the third substrate is combined with the fourth substrate with mirror-symmetry, and the electrical insulating material is arranged between the third substrate and the fourth substrate;
   a light source located at one side of the reagent container holding mechanism, wherein a light emitted by the light source enters into the reagent container and excites the one or more fluorescent probes or fluorescent dyes to generate fluorescence;
   a spectrometer located at one side of the reagent container holding mechanism and configured to detect one or more fluorescent signals of the fluorescence; and
   a processor for quantifying the one or more fluorescent signals, controlling the time points of the heating and cooling periods of the reagent container holding mechanism, and turning on and off the light source.

2. The PCR apparatus according to claim 1, wherein the reagent container holding mechanism including an electric heating apparatus is configured to heating by electrifying to increase the temperature of the reagent container;
the processor is configured to control the temperature of the reagent container holding mechanism to be circulated between a first temperature interval and a second temperature interval to perform PCR using the reactant and the reagent; and the one or more fluorescent signals detected by the spectrometer are transmitted to the processor for analysis.

3. The PCR apparatus according to claim 2, wherein
the PCR apparatus further comprises a heat dissipation apparatus and a temperature sensor which is located at one side of the reagent container holding mechanism and is configured to measure the temperature of the reagent container holding mechanism;

when the temperature of the reagent container holding mechanism detected by the temperature sensor exceeds the first temperature interval, the temperature sensor feeds the information back to the processor, and the processor sends a first signal to the heat dissipation apparatus to lower the temperature; and when the temperature of the reagent container holding mechanism detected by the temperature sensor is lower than the second temperature interval, the temperature sensor feeds the information back to the processor, and the processor sends a second signal to the reagent container holding mechanism to start heating by electrifying.

4. The PCR apparatus according to claim 3, wherein the reagent container holding mechanism is formed by a heat-resistant material, and the temperature of the reagent container holding mechanism is measured in a real-time manner.

5. The PCR apparatus according to claim 3, wherein the heat dissipation apparatus is one selected from the group consisting of one or more fans, one or more thermoelectric (TE) coolers and the combination thereof.

6. The PCR apparatus according to claim 1, wherein the PCR apparatus further comprises a first optical element which is located between the reagent container holding mechanism and the light source, and is capable of guiding the light to the reagent container and to excite the one or more fluorescent probes or fluorescent dyes to generate the fluorescence, and the first optical element and the light source are sequentially arranged under the reagent container holding mechanism.

7. The PCR apparatus according to claim 1, wherein the PCR apparatus further comprises a second optical element which is located between the reagent container holding mechanism and the spectrometer, and is configured to collect the fluorescence, and guide the fluorescence to the spectrometer, and the second optical element and the spectrometer are located on the same horizontal plane.

8. The PCR apparatus according to any one of claims 6 and 7, wherein each of the first and the second optical elements is one selected from the group consisting of a biconvex lens, a plano-convex lens, a doublet lens, an aspheric lens, an achromatic lens, an anastigmatic lens, a Fresnel lens, a plano-concave lens, a biconcave lens, a positive/negative meniscus lens, an axicon, a gradient index lens, a microlens array, a cylindrical lens, a diffractive optical element, a waveguide element, a holographic optical element, a mirror, a fiber and a prism.

9. The PCR apparatus according to claim 1, wherein the first conductive component and the second conductive component are metal sheets or printed circuit boards (PCBs).

10. The PCR apparatus according to claim 9, wherein when the first conductive component and the second conductive component are the metal sheets, each of the first substrate and the second substrate has a surface layer having a conductive thin film thereon, and the conductive thin film is formed of a material being one selected from the group consisting of tin oxide, indium oxide, zinc oxide, indium tin oxide, chromium, titanium, tantalum or copper.

11. The PCR apparatus according to claim 9, wherein when the first conductive component and the second conductive component are the printed circuit boards (PCBs), the printed circuit boards (PCBs) further contain one or more electric heating elements being a resistor or a PCB layout.

12. The PCR apparatus according to claim 1, wherein the first substrate and the second substrate are in parallel arrangement so that the first concave surface and the second concave surface are mutually coupled in a direction roughly perpendicular to the horizontal plane along corresponding coupling surfaces and to form the reagent container holding mechanism.

13. The PCR apparatus according to claim 1, wherein the first substrate has a fluorescent signal outlet window, and the first substrate is located between the second substrate and the spectrometer.

14. The PCR apparatus according to claim 1, wherein the reagent container holding mechanism is formed by a heat-resistant material having one or more heat dissipation holes, the heat-resistant material is a metal capable of rapidly conducting heat being selected from the group consisting of an aluminum sheet, a copper sheet and an alloy thereof.

15. The PCR apparatus according to claim 14, wherein the surface layer of the heat-resistant material contains a heat-resistant insulating material being one selected from the group consisting of aluminum oxide, polytetrafluoroethylene and polyimide.

16. The PCR apparatus according to claim 14, wherein the heat-resistant material is a non-metal being one selected from the group consisting of glass, plastic and ceramic.

17. The PCR apparatus according to claim 1, wherein the light source is one selected from the group consisting of a light emitting diode (LED), a laser source, multiple LEDs of different wavelength, multiple laser sources of different wavelength, and the combination thereof.

18. The PCR apparatus according to claim 1, wherein the processor is configured to control the light source to be turned on or turned off at a specific time interval, and the spectrometer and the light source are turned on to synchronously detect the one or more fluorescent signals.

19. The PCR apparatus according to claim 1, wherein the detection range of the spectrometer is between 340 nm and 850 nm.

20. The PCR apparatus according to claim 1, wherein the PCR apparatus further comprises an optical filter located between the reagent container holding mechanism and the spectrometer, and the optical filter is configured to filter out the light exceeding the wavelength range of the one or more fluorescent signals.

21. The PCR apparatus according to claim 1, wherein the one or more fluorescent probes or fluorescent dyes have a wavelength between 340 nm and 850 nm.

22. The PCR apparatus according to claim 2, wherein the first temperature interval is 85° C. to 130° C., and the second temperature interval is 50° C. to 75° C.

23. The PCR apparatus according to claim 2, wherein the PCR has a third temperature interval different from the first temperature interval and the second temperature interval, and the processor is configured to control the temperature of the reagent container holding mechanism to repeatedly increase and decrease in the cycle of the first temperature interval, the second temperature interval and the third temperature interval.

\* \* \* \* \*